(12) United States Patent
Tears et al.

(10) Patent No.: US 6,936,038 B2
(45) Date of Patent: Aug. 30, 2005

(54) ABSORBENT ARTICLE HAVING A PAIR OF FRINGES

(75) Inventors: Denise Crites Tears, Appleton, WI (US); Amanda Lee O'Connor, Neenah, WI (US); Russell Gerald Mayer, Appleton, WI (US); Stephen Alan Kolasinski, Appleton, WI (US); Wendy Jean Wegner, Appleton, WI (US); Chad Krueger, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 446 days.

(21) Appl. No.: 10/081,852

(22) Filed: Feb. 22, 2002

(65) Prior Publication Data

US 2003/0163105 A1 Aug. 28, 2003

(51) Int. Cl.⁷ .............................................. A61F 13/15
(52) U.S. Cl. ...................... 604/385.04; 604/385.101; 604/385.28
(58) Field of Search ................... 604/385.03–385.04, 604/385.101, 385.28, 368

(56) References Cited

U.S. PATENT DOCUMENTS

| | | |
|---|---|---|
| 2,064,431 A | 12/1936 | Jurgensen |
| 2,787,271 A | 4/1957 | Clark |
| 3,395,201 A | 7/1968 | Kalwaites |
| 3,411,504 A | 11/1968 | Glassman |
| 3,559,650 A | 2/1971 | Larson |
| 3,575,174 A | 4/1971 | Mogor |
| 3,635,221 A | 1/1972 | Champaigne |
| 3,886,941 A | 6/1975 | Duane et al. |
| 3,888,255 A | 6/1975 | Shah et al. |
| 4,059,114 A | 11/1977 | Richards |
| 4,204,532 A | 5/1980 | Lind et al. |
| 4,215,692 A | 8/1980 | Levesque |
| 4,324,245 A | 4/1982 | Mesek et al. |
| 4,589,876 A | 5/1986 | Van Tilburg |
| 4,627,847 A | 12/1986 | Puletti et al. |
| 4,655,759 A | 4/1987 | Romans-Hess et al. |
| 4,690,680 A | 9/1987 | Higgins |
| 4,692,161 A | 9/1987 | Puletti et al. |
| 4,718,898 A | 1/1988 | Puletti et al. |
| 4,770,657 A | 9/1988 | Ellis et al. |
| 4,773,904 A | 9/1988 | Nakanishi et al. |
| 4,834,739 A | 5/1989 | Linker, III et al. |
| 4,911,701 A | 3/1990 | Mavinkurve |
| 4,938,756 A | 7/1990 | Salek |
| 5,011,480 A | 4/1991 | Gossens et al. |
| 5,197,959 A | 3/1993 | Buell |
| 5,221,275 A * | 6/1993 | Van Iten ..................... 604/387 |
| 5,234,422 A | 8/1993 | Sneller et al. |
| 5,236,428 A | 8/1993 | Zajaczkowski |
| 5,300,058 A | 4/1994 | Goulait et al. |
| 5,312,386 A | 5/1994 | Correa et al. |

(Continued)

FOREIGN PATENT DOCUMENTS

| | | |
|---|---|---|
| EP | 0 464 854 B1 | 8/1991 |
| EP | 0 687 453 A1 | 12/1995 |
| EP | 0 945 110 A2 | 9/1999 |
| FR | 2 423 171 | 11/1979 |
| GB | 2 233 235 A | 1/1991 |

*Primary Examiner*—Larry I. Schwartz
*Assistant Examiner*—C. Lynne Anderson

(57) ABSTRACT

An absorbent article is disclosed having an absorbent with first and second longitudinal sides. A liquid permeable wrapper encloses the absorbent. The wrapper extending laterally outward from each of the first and second longitudinal sides a distance of at least about 10 millimeters to form a pair of fringes. The pair of fringes are capable of being biased upward to form a pair of upstanding side walls when the absorbent article is placed in an undergarment. The upstanding side walls form a pair of reservoirs located adjacent to the absorbent. The reservoirs are capable of retaining body fluid that has run off of the wrapper until the body fluid can be absorbed by the absorbent.

20 Claims, 6 Drawing Sheets

U.S. PATENT DOCUMENTS

| | | | |
|---|---|---|---|
| 5,356,403 A | * 10/1994 | Faulks et al. ............... 604/378 |
| 5,391,162 A | 2/1995 | Widlund et al. |
| 5,401,266 A | 3/1995 | Runeman et al. |
| 5,454,804 A | 10/1995 | Widlund |
| 5,489,283 A | 2/1996 | Van Tillburg |
| 5,516,567 A | * 5/1996 | Roessler et al. ........... 428/40.1 |
| 5,624,423 A | 4/1997 | Anjur et al. |
| 5,649,917 A | 7/1997 | Roberts et al. |
| 5,704,928 A | * 1/1998 | Morita et al. .......... 604/385.23 |
| 5,778,457 A | 7/1998 | Conway |
| H1746 H | 8/1998 | Carrier et al. |
| 5,795,344 A | 8/1998 | Chappell |
| 5,820,618 A | 10/1998 | Roberts et al. |
| 5,843,056 A | 12/1998 | Good et al. |
| 5,879,341 A | 3/1999 | Odorzynski et al. |
| 6,229,061 B1 | 5/2001 | Dragoo et al. |
| 6,371,948 B1 | * 4/2002 | Mizutani ............... 604/385.01 |
| 6,689,113 B2 | 2/2004 | Boulanger et al. |
| 2003/0116888 A1 | 6/2003 | Rymer et al. |
| 2003/0119402 A1 | 6/2003 | Melius et al. |

* cited by examiner

ABSORBENT ARTICLE HAVING A PAIR OF FRINGES

BACKGROUND OF THE INVENTION

Today, many different forms of primary absorbent undergarments, diapers and fitted briefs are available to consumers who experience urinary incontinence. Some of these products are designed to resemble common cotton underwear except that they contain a highly absorbent material. Many of these products are have a design that does not fully prevent fluid leakage. In addition, even though such products are relatively inexpensive, many people who use such products, especially the elderly, are interested in lower cost alternatives. One solution to this problem is to attach an inexpensive absorbent article, diaper insert or liner within the primary absorbent undergarment. When the absorbent article is saturated with urine, it can easily be removed and discarded. Another absorbent article, diaper insert or liner can then be inserted into the primary absorbent undergarment so as to prolong the life of the primary absorbent undergarment. The absorbent article, diaper insert or liner is substantially less costly than the primary absorbent undergarment.

The absorbent article of this invention differs in construction from current commercially available incontinence pads or liners in that it exhibits the ability to allow urine and other body fluid to pass readily therethrough and enter the primary absorbent undergarment under controlled conditions. The absorbent article is also capable of limiting side leakage of body fluid.

Now an inexpensive absorbent article for absorbing body fluids has been invented which is designed to allow the body fluid to pass readily therethrough and reduce fluid leakage onto the consumers clothing while effectively prolonging the useful life of a primary absorbent undergarment.

SUMMARY OF THE INVENTION

Briefly, this invention relates to an absorbent article having an absorbent with first and second longitudinal sides. A liquid permeable wrapper encloses the absorbent. The wrapper extends laterally outward from each of the first and second longitudinal sides a distance of at least about 10 millimeters to form a pair of fringes. The pair of fringes are capable of being biased upward to form a pair of upstanding side walls when the absorbent article is placed in an undergarment. The upstanding side walls form a pair of reservoirs located adjacent to the absorbent. The reservoirs are capable of retaining body fluid that has run off of the wrapper until the body fluid can be absorbed by the absorbent.

DETAILED DESCRIPTION

Figure 1:
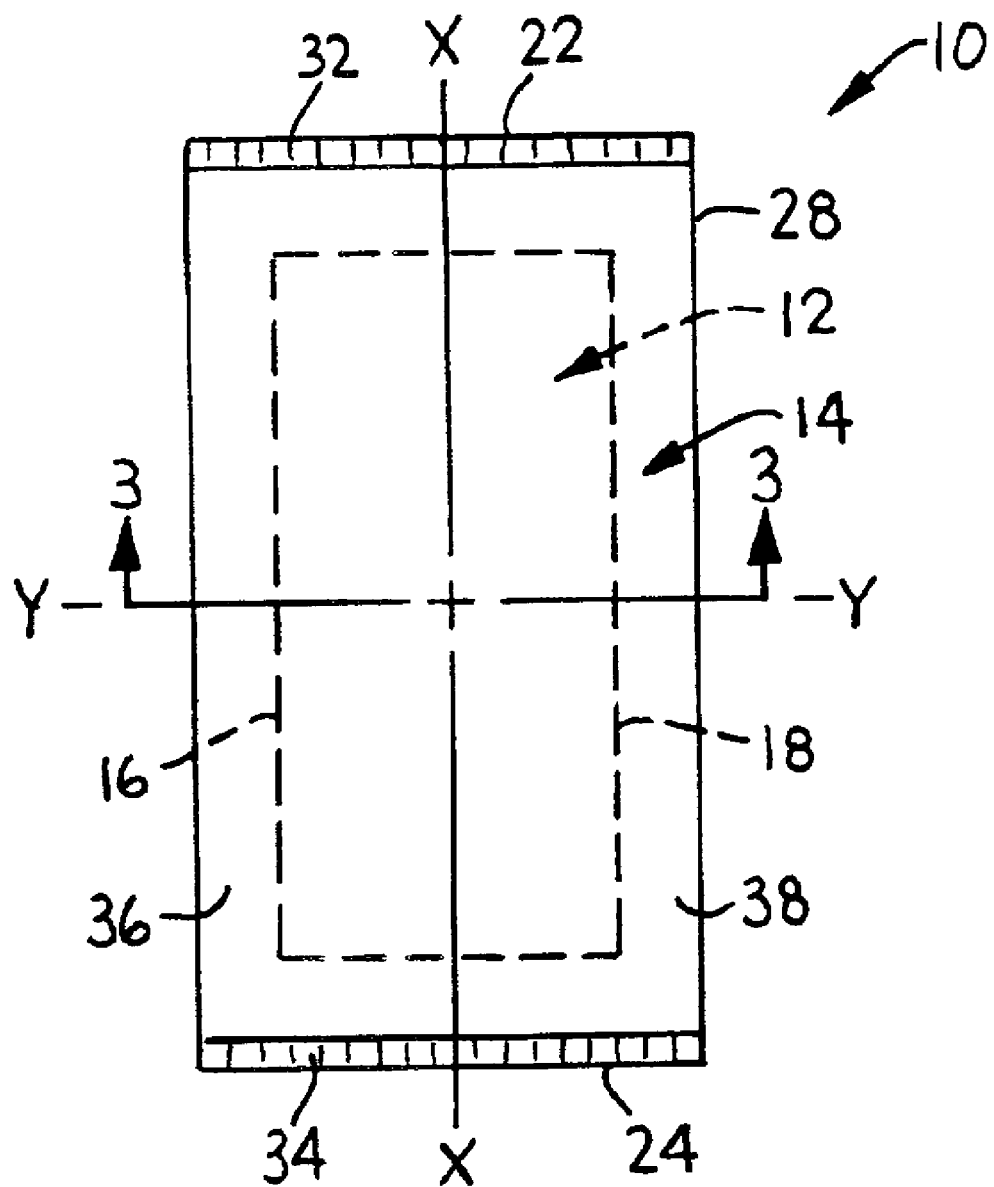
FIG. 1 is a top view of an absorbent article for urinary incontinence.
Figure 2:
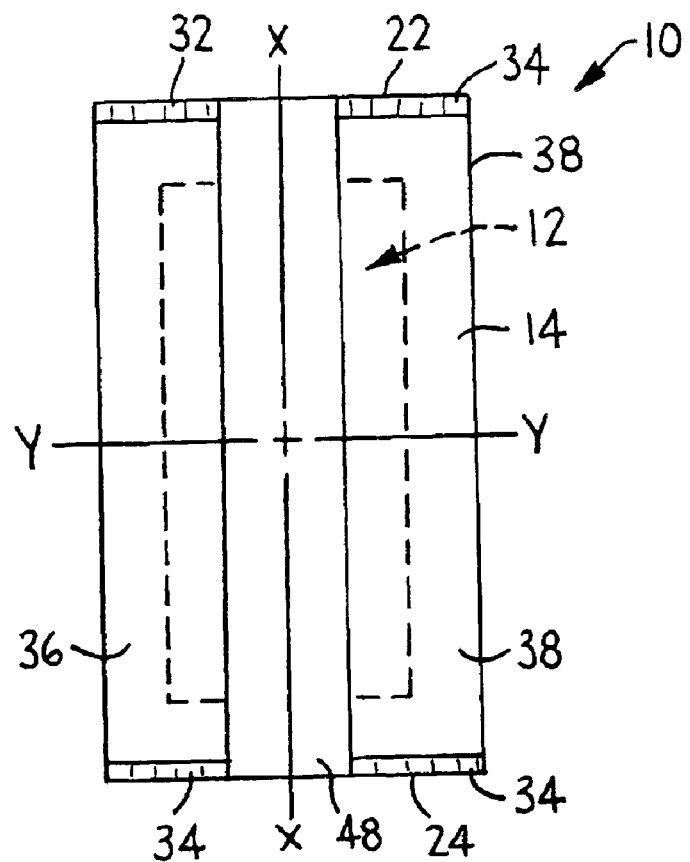
FIG. 2 is a bottom view of the absorbent article shown in FIG. 1.
Figure 3:
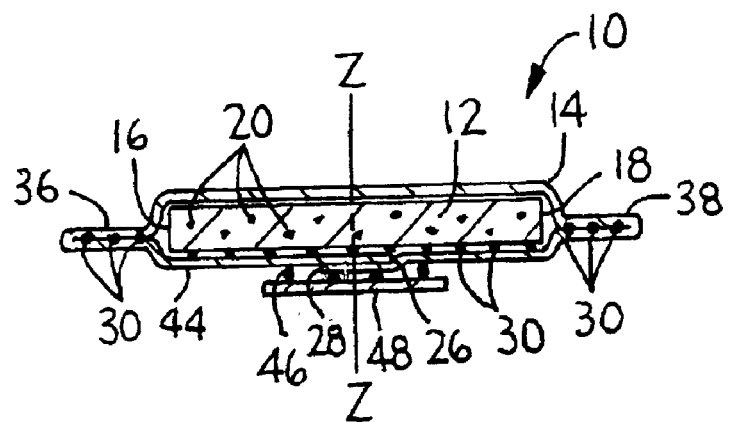
FIG. 3 is a cross-sectional view the absorbent article shown in FIG. 1 taken along line 3—3.
Figure 4:
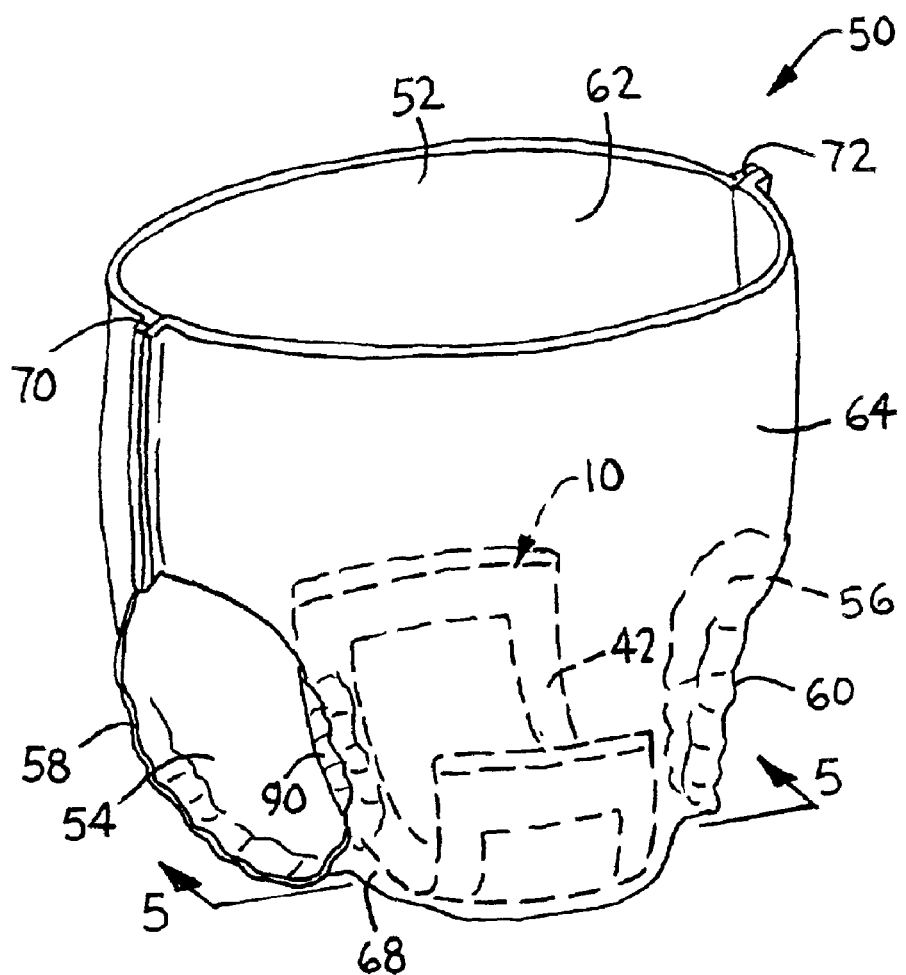
FIG. 4 is a perspective view of the absorbent article positioned in the crotch portion of an absorbent undergarment.

Referring to FIGS. 1–3, an absorbent article 10, such as a urinary incontinence pad, a diaper insert or a liner, is shown which is capable of absorbing a relatively large quantity of urine. The absorbent article 10 includes an absorbent 12 enclosed by a liquid permeable wrapper 14. The absorbent article 10 is an elongated member having a longitudinal axis x—x, a transverse axis y—y and a vertical axis z—z. The absorbent article 10 can have a rectangular, hourglass, racetrack, oval, elliptical or other geometrical configuration when viewed from the top. Suitably, the absorbent article 10 has a rectangular configuration. The absorbent article 10 has a length, measured parallel to the longitudinal axis x—x, of less than about 500 millimeters (mm). Desirably, the absorbent article 10 has a length of less than about 400 mm, and most desirably, a length of less than about 350 mm. The absorbent article 10 has a crotch width, measured parallel to the transverse axis y—y, of less than about 150 mm. Desirably, the crotch width of the absorbent article 10 is less than about 125 mm, and most preferably, the crotch width of the absorbent article 10 is less than about 110 mm. The absorbent article 10 has a height, measured parallel to the vertical axis z—z of from about 2 mm to about 25 mm, and preferably, less than about 18 mm.

The absorbent 12 is an elongated member having a first longitudinal side 16 and a second longitudinal side 18. The first and second longitudinal sides, 16 and 18 respectively, are aligned approximately parallel to the longitudinal axis x—x. Like the absorbent article 10, the absorbent 12 is depicted having a rectangular configuration. However, the absorbent 12 can be constructed to have some other shape, including an hourglass shape, an oval shape, a racetrack shape, an elliptical shape, etc. The absorbent 12 is shown as a single layer in FIG. 3, however, the absorbent 12 can consist of one or more absorbent layers. The absorbent 12 can be made from natural or synthetic fibers, including cellulose fibers, surfactant-treated meltblown fibers, wood pulp fibers, regenerated cellulose or cotton fibers, coform or from other absorbent materials known to those skilled in the art. The absorbent 12 can also be made from a combination of two or more absorbent materials. Coform is a blend of pulp and synthetic meltblown fibers. Two desirable absorbent materials from which the absorbent 12 can be constructed are wood pulp fluff and coform.

The absorbent 12 can contain a hydrocolloidal material 20, commonly referred to as a superabsorbent. The superabsorbent 20 can be a partially neutralized salt of polyacrylic acid.

A superabsorbent is normally added to the absorbent 12 to increase the amount of fluid that the absorbent 12 can absorb and retain. The fluid retention capacity, also referred to as fluid absorbent capacity, of the absorbent 12 for urine should be at least 150 grams (g). Desirably, the fluid absorbent capacity of the absorbent 12 for urine is at least 200 g. Most desirably, the fluid absorbent capacity of the absorbent 12 is at least 250 g. It should be noted that saline is normally used in place of human urine when measuring the fluid retention or absorbent capacity of the absorbent 12. Saline is an aqueous solution of about 0.9% sodium chloride by weight. One brand of saline is S/P® Certified Blood Saline, which is commercially available from Baxter Diagnostics having an office in McGraw Park, Ill. The reason for using saline instead of actual human urine is that it is sanitary to handle in a laboratory. In addition, the absorbency results for an absorbent core tested using about 0.9% saline is very close to the absorbency results using human urine.

The superabsorbent 20 that can be added to the absorbent 12 can be produced to have almost any physical form. Commonly, the superabsorbent 20 is in the shape of small particles having a major dimension of less than about 500 microns. Superabsorbents are commercially available from several different vendors including Dow Chemical Company, Hoechst-Celanese and Stockhausen Inc. Two superabsorbents that work well for retaining urine are DRYTECH® 2035M and FAVORS® SXM 880. DRYTECH® 2035M is available from Dow Chemical Company having a mailing address of P.O. Box 846028 Dallas, Tex. 75284-6028. FAVOR® SXM 880 is available from Stockhausen Inc. having a mailing address of P.O. Box 7247-7261 Philadelphia, Pa. 19170-7261.

It should also be noted that the absorbent 12 can be formed as a laminate structure with the superabsorbent 20 incorporated therein.

Referring to FIG. 3, the absorbent 12 has a height, measured parallel to the vertical axis z—z, of from about 2 mm to about 25 mm. Desirably, the absorbent 12 has a height of from about 3 mm to about 20 mm. Most desirably, the absorbent 12 has a height of from about 4 mm to about 15 mm. As the height of the absorbent 12 increases, the fluid capacity of the absorbent 12 normally increases. However, it will be appreciated that the materials from which the absorbent 12 is constructed, the presence of the superabsorbent 20, and the thickness of the absorbent 12 will all cooperate to determine the fluid capacity of the absorbent 12.

The liquid permeable, wrapper 14 encloses the absorbent 12. By "liquid permeable" it is meant that body fluids, such as urine, blood, menses, etc., and vapors can quickly pass therethrough and be received by the absorbent 12. The wrapper 14 will directly contact the genital area of the wearer when the absorbent article 10 is fitted against the wearer's torso. The wrapper 14 functions to allow such body fluid to pass downward into the absorbent 12. The liquid permeable wrapper 14 can be constructed from a natural or a synthetic material. The wrapper 14 can be formed from a woven or a nonwoven material. Suitable materials include bonded-carded webs of polyester, polypropylene, polyethylene, nylon or other heat-bondable fibers, as well as other materials known to those skilled in the art. Other polyolefins, such as copolymers of polypropylene and polyethylene, linear low-density polyethylene, finely perforated film webs and net materials also work well. A desired material is spunbond. Spunbond is a nonwoven material formed from polypropylene fibers. Spunbond is sold commercially by Kimberly-Clark Corporation having an office at 401 North Lake Street, Neenah, Wis. 54956. The spunbond is treated to be hydrophilic so as to allow liquid to penetrate therethrough. The spunbond can contain from about 1% to about 2% titanium dioxide pigment to give it a clean, white appearance.

The wrapper 14 can be formed from a material having a variety of basis weights. When the wrapper 14 is formed from spunbond, the material can have a basis weight of from about 0.3 ounces per square yard (osy) to about 1.0 osy. Desirably, the basis weight for the spunbond material is from about 0.3 osy to about 0.5 osy. Most desirably, the basis weight of the spunbond material should be about 0.385 osy.

The liquid permeable wrapper 14 should allow body fluids, especially urine, that contacts it to readily and quickly pass therethrough. In this regard, the material from which the wrapper 14 is constructed is selected to have pores or openings that permit liquids and/or gases to pass therethrough. The liquid permeability of the wrapper 14 can be measured using a common test procedure known to those skilled in the art.

Referring again to FIGS. 1, 2 and 3, the liquid permeable wrapper 14 has a first end 22 spaced apart from and a second end 24. The liquid permeable wrapper 14 also has a first side edge 26 spaced apart from a second side edge 28, see FIG. 3. The wrapper 14 can be C-folded around the absorbent 12 such that the second side edge 28 overlaps the first side edge 26, as shown. Alternatively, the first and second side edges, 26 and 28 respectively, can abut one another, if desired. It should be noted that the C-fold is aligned along the longitudinal axis x—x and the first and second side edges are aligned approximately parallel to the longitudinal axis x—x.

Referring again to FIG. 3, the wrapper 14 can be secured to itself and/or to one or more surfaces of the absorbent 12 by a construction adhesive 30. Other types of attachment means can also be utilized. In FIG. 3, the construction adhesive 30 is shown securing the wrapper 14 to the lower surface of the absorbent 12. The construction adhesive 30 can be either a hot melt adhesive or a cold melt adhesive. A hot melt adhesive that works well is REXTAC® RT 2730. This construction adhesive is commercially available from Huntsman Polymers Corporation having a mailing address of P.O. Box 371263 Pittsburgh, Pa. 15251-7263.

Referring again to FIG. 1, one will notice that the absorbent 12 has a length, measured parallel to the longitudinal axis x—x, that is shorter than the length of the wrapper 14. This is important for it is necessary for the wrapper 14 to completely enclose the absorbent 12 and form an integral product. When the absorbent article 10 includes an absorbent 12 having superabsorbent particles 20 contained therein, the wrapper 14 will ensure than the superabsorbent particles 20 can not be released. The first and second ends, 22 and 24 respectively, of the absorbent article 10 will extend beyond the length of the absorbent 12. Each of the first and second ends, 22 and 24 respectively, is sealed. The wrapper 14 can be sealed at each end 22 and 24 by an ultrasonic bond. Other methods of sealing the first and second ends, 22 and 24 respectively, include forming a pressure bond, a heat bond, a heat and pressure bond, using a hot or cold melt adhesive, using thread, etc. These and other methods are known to those skilled in the art.

In FIGS. 1 and 2, a first seal 32 is formed at the first end 22 of the wrapper 14 by using adhesives or ultrasonics. The first seal 32 can have a variety of bond patterns. However, the bond pattern of the first seal 32 should have a dimension, measured along the longitudinal axis x—x, of from about 10 millimeters (mm) to about 30 mm. More desirably, the bond pattern of the first seal 32 will have a dimension, measured along the longitudinal axis x—x of from about 12 mm to about 25 mm. Most desirably, the bond pattern of the first seal 32 will have a dimension, measured along the longitudinal axis x—x, of from about 15 mm to about 20 mm.

A second seal 34 is formed at the second end 24 of the wrapper 14 by using adhesives or ultrasonics. The second seal 34, like the first seal 32, can have a variety of bond patterns. However, the bond pattern of the second seal 34 can have a dimension, measured along the longitudinal axis x—x, of from about 10 millimeters (mm) to about 30 mm. More desirably, the bond pattern of the second seal 34 will have a dimension, measured along the longitudinal axis x—x, of from about 12 mm to about 25 mm. Most desirably, the bond pattern of the second seal 34 will have a dimension, measured along the longitudinal axis x—x, of from about 15 mm to about 20 mm.

Referring now to FIGS. 1–5, one will notice that the wrapper 14 has a pair of fringes 36 and 38 (see FIGS. 1–3) which extends laterally outward from each of said first and second longitudinal sides, 16 and 18 respectively, of the absorbent 12. Each of the pair of fringes 36 and 38 may contain one or more beads, strands or a swirl pattern of the construction adhesive 30, see FIG. 3. Each of the pair of fringes 36 and 38 runs the entire length of the absorbent article 10. Each of the pair of fringes 36 and 38 has a width dimension, measured parallel to the transverse axis y—y that extends laterally outward from one of the first or second longitudinal sides, 16 and 18 respectively, by a distance of at least 10 mm. Desirably, each of the pair of fringes 36 and 38 has a width dimension that extend laterally outward from one of the first or second longitudinal sides, 16 and 18 respectively, by a distance of from about 10 mm to about 30 mm. More desirably, each of the pair of fringes 36 and 38 has a width dimension that extend laterally outward from one of the first or second longitudinal sides, 16 and 18 respectively, by a distance of from about 12 mm to about 20 mm. The pair of fringes 36 and 38 are capable of being biased upward to form a pair of upstanding side walls 40 and 42, see FIGS. 4 and 5.

Figure 5:
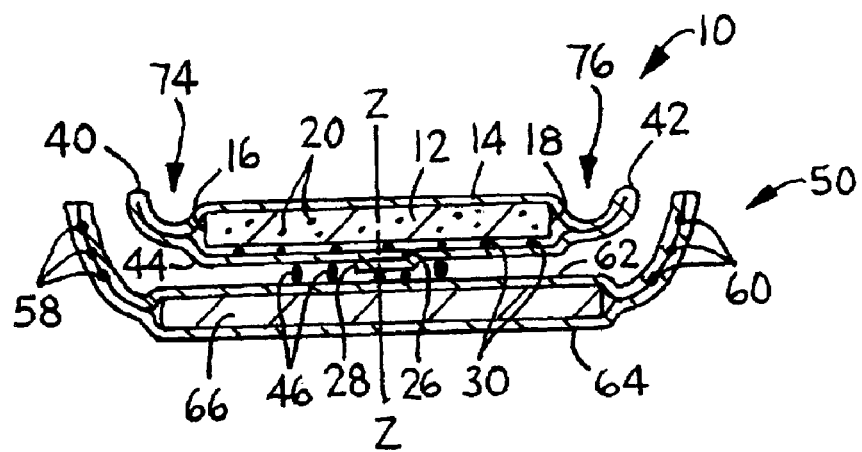
FIG. 5 is a cross-sectional view of the combination absorbent article and absorbent undergarment shown in FIG. 4 taken along line 5—5 and depicting the upstanding side walls of the absorbent article forming a pair of reservoirs positioned adjacent to the absorbent core.

Referring to FIGS. 3 and 5, one will notice that the pair of fringes 36 and 38 do not contain any elastic components, such as elastic threads, strands, etc. Another way of expressing this is to say that the pair of fringes 36 and 38 are free or void of any elastic. One reason for this is that the pair of fringes 36 and 38 do not require elastic materials to make them act as upstanding side walls. The pair of fringes 36 and 38 also do not require a high degree of stiffness in order to stand up. Although the pair of fringes 36 and 38 may contain one or more lines or beads of construction adhesive 30, they are still relatively flexible.

As shown in FIGS. 3 and 5, the wrapper 14 is the only material, besides the adhesive 30, used to form the pair of fringes 36 and 38. By folding or doubling the wrapper 14 upon itself, the pair of fringes 36 and 38 are formed. The pair of fringes 36 and 38 are very flexible, pliable and bendable. The pair of fringes 36 and 38 are also receptive to acquiring an upward configuration when inserted into an undergarment which is arranged about the torso of the wearer.

Still referring to FIGS. 3 and 5, the wrapper 14 has an exterior surface 44. Secured to the exterior surface 44 is an attachment means 46. The attachment means 46 is preferably a garment adhesive. Other forms of attachment mechanisms that can be utilized include hook and/or loop fasteners, tape, glue, etc. VELCRO® is one form of a hook fastener that engages a loop material. A superabsorbent is normally added to the absorbent core 80 to increase the amount of fluid that the absorbent core 80 can absorb and retain. The fluid retention capacity, also referred to as fluid absorbent capacity, of the absorbent core 80, for urine, should be at least 150 grams (g). Desirably, the fluid absorbent capacity of the absorbent core 80 for urine is at least 200 g. Most desirably, the fluid absorbent capacity of the absorbent core 16 for urine is at least 250 g.

When the attachment means 46 is a garment adhesive, the adhesive can be either a hot or cold melt adhesive that is sprayed, brushed, slot coated or otherwise secured onto the exterior surface 44 of the wrapper 14. The garment adhesive can be applied as one or more beads, lines or strips of adhesive aligned approximately parallel to the longitudinal axis x—x. Preferably, the garment adhesive is a hot melt adhesive. Garment adhesive is commercially available from several vendors. One such vendor is National Starch Co. having an office at 10 Finderne Avenue, Bridgewater, N.J. 08807.

When VELCRO® is used as the attachment means 46, the hook portion can be secured to a portion of the wrapper 14 and the loop portion can be secured to a portion of the primary absorbent undergarment 50 or vice versa. It should also be noted that some materials, like spunbond, can serve the same function as a loop material and therefore a separate patch of loop material does not have to be secured opposite to the hook material. For example, if a patch of hook material is secured to the wrapper 14, the primary absorbent undergarment 50 will not be required to have a patch of loop material secured to it.

As mentioned above, the wrapper 14 has an exterior surface 44 and a portion of this exterior surface 44 will contact the primary absorbent undergarment 50. The portion of the exterior surface 44 that will contact the primary absorbent undergarment 50 can be formed to have a high coefficient of friction making it a non-skid surface. For example, the exterior surface 44 can consist of a roughened surface, a treated surface or be made from a non-skid material. The roughened, treated or non-skid surface will provide a physical attachment to the primary absorbent undergarment 50. Another way of stating this is to say that the non-skid portion of the exterior surface 44 serves a similar function as the attachment means 46.

A releasable peel strip 48 can be positioned over the attachment means 46. The releasable peel strip 48 protects the attachment means 46 from contamination prior to use of the absorbent article 10 by the consumer. The releasable peel strip 48 is designed to be removed by the consumer just prior to positioning and attaching the absorbent article 10 to the crotch portion of a primary absorbent undergarment. The peel strip 48 is generally slightly larger in overall dimensions than the attachment means 46 so as to avoid registration problems when the absorbent article 10 is being manufactured. The use of a slightly larger dimensioned peel strip 48 to cover the attachment means 46 is particularly advantageous when the absorbent article 10 are being produced at relatively high speeds. By "high speeds" is meant the ability to manufacture the absorbent article 10 at a speed of more than 200 absorbent articles per minute. The peel strip 48 can be a white Kraft paper, coated on one side by silicone so that it can be easily released from the attachment means 46.

Returning to FIG. 2, one will notice that the peel strip 48 extends the entire length of the absorbent article 10. By sizing the peel strip 48 to have the same length as the absorbent article 10, one can increase manufacturing speeds. The reason for this is that the peel strip 48 and the absorbent article 10 can be cut together and one does not have to register or center the overall length of the peel strip 48 to the absorbent article 10. However, one can use a shorter peel strip, if desired. The use of a shorter length of peel strip 48 can reduce the cost of manufacturing the absorbent article 10.

Returning again to FIGS. 4 and 5, a primary absorbent undergarment 50 is shown having a waist opening 52 and a pair of leg openings 54 and 56. Each of the pair of leg openings 54 and 56 can be elasticized, if desired, by incorporating one or more strands of elastic, 58 and 60 respectively. The primary absorbent undergarment 50 has a liquid permeable bodyside cover 62, a liquid-impermeable baffle 64, and an absorbent 66 positioned therebetween. The bodyside cover 62 is designed to allow rapid intake of body fluid. The cover 62 can be constructed of a woven or nonwoven material formed from either natural or synthetic fibers that can easily be penetrated by body fluids. Suitable materials include bonded-carded webs of polyester, polypropylene, polyethylene, nylon or other heat-bondable fibers, as well as other materials known to those skilled in the art. Other polyolefins, such as copolymers of polypropylene and polyethylene, linear low-density polyethylene, finely perforated film webs and net materials, also work well.

The primary absorbent undergarment 50 has a crotch portion 68 formed between the pair of leg openings, 54 and 56 respectively. The primary absorbent undergarment 50 is depicted as having a pair of side seams 70 and 72 that can be manually torn open. The presence of the side seams 70 and 72 are not required. The undergarment 50 can be pulled up onto the wearer's torso in a similar fashion as regular cotton underwear. For removal, the wearer can pull the undergarment 50 down in a similar fashion as regular cotton underwear or one or both of the side seams 70 and 72 can be torn open for easy removal.

It should be noted that the primary absorbent undergarment 50 could be formed with a refastenable waist design such that the waist can be opened and closed more than once. Such a design is advantageous in allowing the consumer to tighten or loosen the primary absorbent undergarment 50 around his or her waist.

The primary absorbent undergarment 50 can be in the form of a pant product, a brief product, an undergarment product, a diaper, a menstrual panty, etc. These terms are used to identify differently configured absorbent products. The primary absorbent undergarment 50 is preferably a disposable product that will be discarded after a single use. However, the primary absorbent undergarment 50 could also be a disposable undergarment that is designed for multiple uses. The primary absorbent undergarment 50 is not made to be laundered. However, the primary absorbent undergarment 50 can be a non-disposable undergarment that can be laundered one or more times before being discarded. Still further, the primary absorbent undergarment 50 can be an undergarment that has a pocket or fold for containing a disposable insert or liner. Any and all such absorbent undergarments are capable of being used in conjunction with the absorbent article 10.

The liquid-impermeable baffle 64 on the primary absorbent undergarment 50 functions to prevent body fluid from passing therethrough. The liquid-impermeable baffle 64 can be made from a micro-embossed polymeric film, such as polyethylene or polypropylene, or it can be made from bicomponent films. A preferred material is polyethylene having a thickness of less than about 3 mm.

The absorbent article 10 is attached to the bodyside cover 62 of the primary absorbent undergarment 50 by the attachment means 46. Usually, the wearer will place or position the crotch portion of the absorbent article 10 over at least a portion of the crotch portion 68 of the primary absorbent undergarment 50. The comfort to the wearer and the location of where the absorbent article 10 will be insulted with body fluid will dictate the exact placement of the absorbent article 10 in the undergarment 50. The absorbent article 10 can be attached to the primary absorbent undergarment 50 before the undergarment 50 is positioned onto the wearer's body. Alternatively, the absorbent article 10 can be attached to the primary absorbent undergarment 50 when the undergarment 50 is positioned about the shins, knees or thighs of the wearer. It is also possible for a caregiver to position the primary absorbent undergarment 50, in an open configuration, about the wearer's torso and then attach the absorbent article 10 before the primary absorbent undergarment 50 is closed and/or fastened around the wearer's waist.

As the absorbent article 10 is secured to the bodyside cover 62 of the primary absorbent undergarment 50, it acquires a cup shape or curvature due to the configuration of the primary absorbent undergarment 50. This cup shape or curvature causes the pair of fringes 36 and 38 to be biased upward and forms the pair of upstanding side walls 40 and 42. Each of the side walls, 40 and 42 respectively, is free of elastics. It is not necessary that stretchable material or material that can extend or contract in at least one direction be present in the side walls 40 and 42 in order to make the side walls 40 and 42 stand upright. The combination of the curvature of the crotch portion 68 of the primary absorbent undergarment 50 and the width dimension of each of the pair of fringes 36 and 38 allow the pair of side walls 40 and 42 to acquire an upright orientation.

Each of the pair of upstanding side walls 40 and 42 forms a reservoir, 74 and 76 respectively, located adjacent to and outward from the absorbent 12. The reservoirs 74 and 76 are capable of retaining body fluid that has run off of the wrapper 14 until the body fluid can be absorbed by the absorbent 12. The construction of the absorbent article 10 and the width dimension of the pair of fringes 36 and 38 will dictate the depth of each of the pair of reservoirs 74 and 76. The pair of fringes 36 and 38 can be sized to be less than, equal to or be greater than the height of the absorbent 12. In FIG. 5, each of the side walls 40 and 42 have sufficient height to hold any body fluid that pooled on the wrapper 14 and has run laterally off to one or both sides. The pair of reservoirs 74 and 76 should also have a length that extends along at least a portion of the middle of the absorbent article 10 when measured along the longitudinal axis x—x. Preferably, each of the pair of reservoirs 74 and 76 will have a length that extends along a portion of the length of the absorbent 12. Depending upon the size of the absorbent article 10, each of the pair of reservoirs 74 and 76 should have a length of greater than about 1 inch (about 25.4 mm). More preferably, each of the pair of reservoirs 74 and 76 should have a length of greater than about 2 inches (about 51 mm). Most preferably, each of the pair of reservoirs 74 and 76 should have a length of greater than about 3 inches (about 76 mm).

The absorbent article 10 can be visualized as an absorbent structure that is used to extend and prolong the useful life of the primary absorbent undergarment 50. Since the primary absorbent undergarment 50 is more costly than the absorbent article 10, the consumer can extend the life of the primary absorbent article 50 for a relatively small amount of money. It is also possible for the consumer to sequentially change the original absorbent article 10, when wetted, with another absorbent article 10. This will enable the wearer to extend the time period before the primary absorbent undergarment 50 becomes so saturated with urine that it needs to be discarded.

It should be noted that the purpose of the absorbent article 10 is to receive and retain body fluid, especially urine. The absorbent article 10 is constructed with a liquid permeable wrapper 14 so as to permit urine to pass quickly down into the absorbent 12. Excess urine that cannot be retained by the absorbent 12 and/or the superabsorbent 20 will move downward through that portion of the wrapper 14 that is located below the absorbent 12. This excess urine will then contact the primary absorbent undergarment 50 and be retained therein. However, if the absorbent article 10 is insulted with urine at a very slow rate, the absorbent article 10 may be able to absorb and retain essentially all of the urine expelled from the wearer. In this situation, the wearer can remove the initial absorbent article 10 that has become saturated and replace it with another dry absorbent article 10. By doing so, the wearer will extend the wearing time of the primary absorbent undergarment 50.

It is also possible to insert two or more absorbent articles 10 into the undergarment 50 at the same time. This will further prolong the life of the undergarment 50. Preferably, one absorbent article 10 will be aligned vertically above the second absorbent article 10. By using two or more absorbent articles 10 at the same time, one can further extend or prolong the life of the primary absorbent undergarment 50. When the upper most absorbent article 10 becomes saturated with body fluid, it can be removed. It is possible to replace the upper most absorbent article 10 at this time with a new dry absorbent article 10, if desired.

Figure 6:
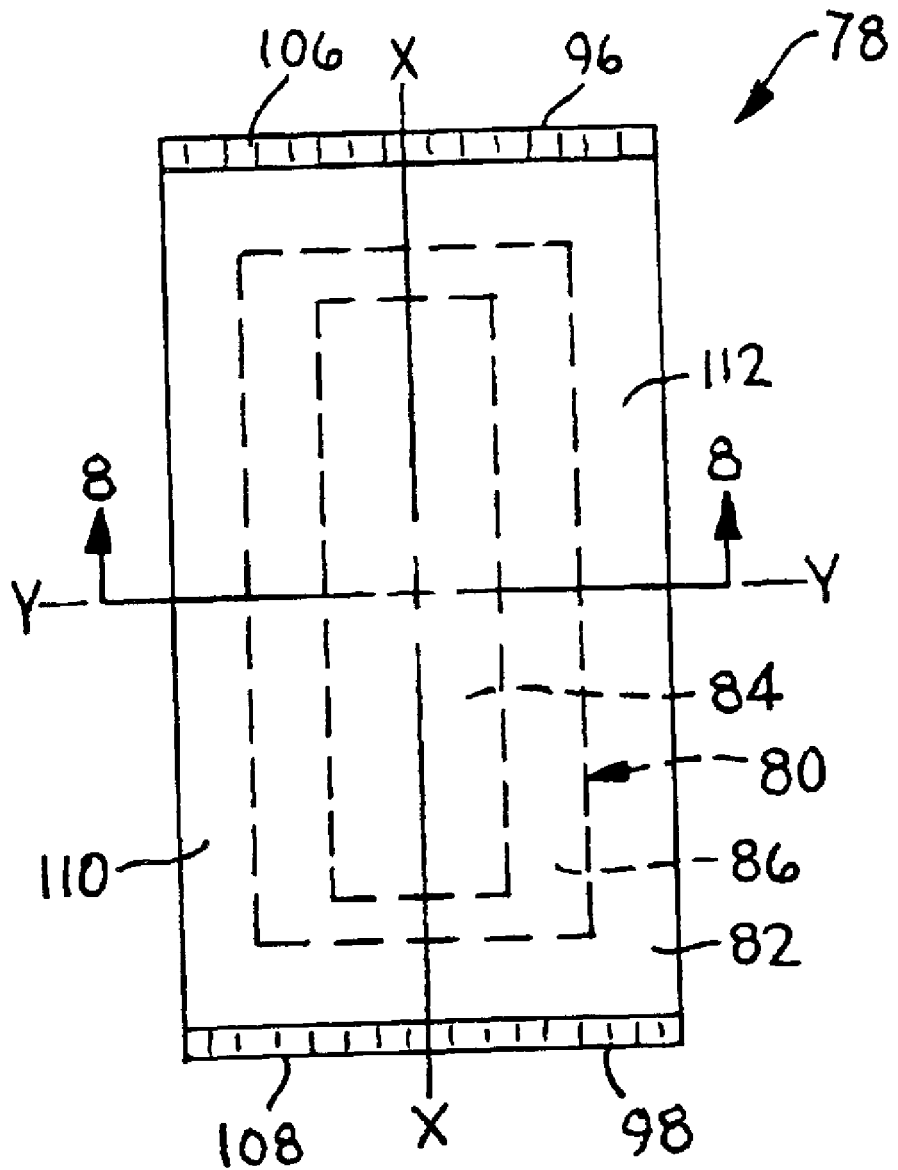
FIG. 6 is a top view of an alternative absorbent article for urinary incontinence having a two layer absorbent core.
Figure 7:
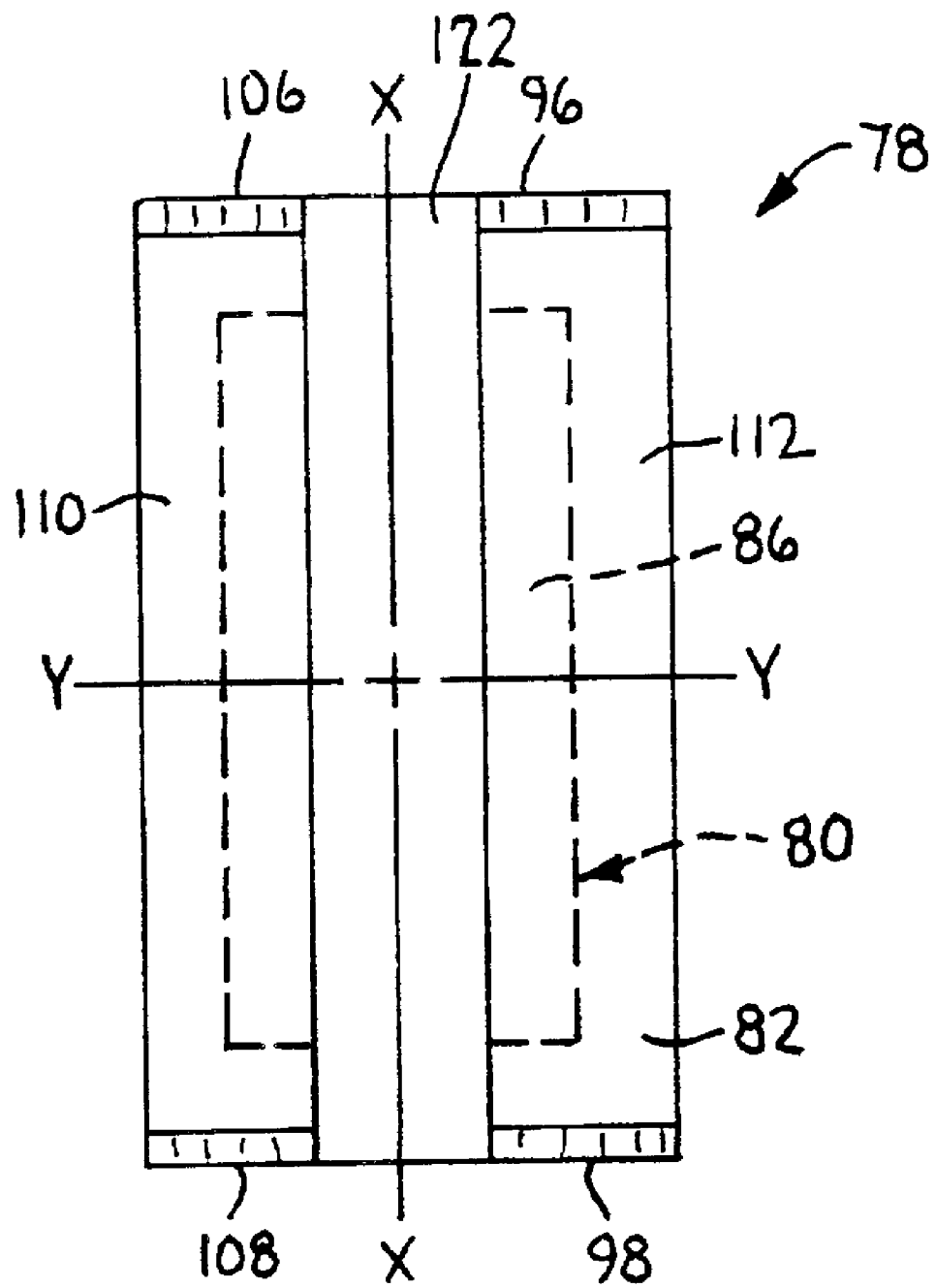
FIG. 7 is a bottom view of the absorbent article shown in FIG. 6.
Figure 8:
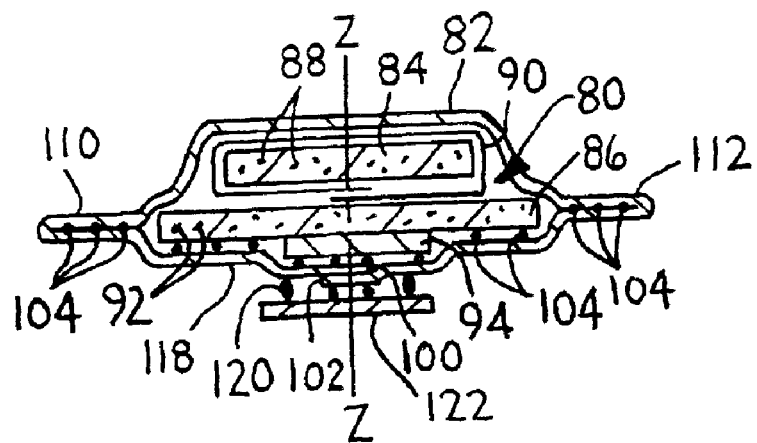
FIG. 8 is a cross-sectional view of the absorbent article shown in FIG. 6 taken along line 8—8.

Referring now to FIGS. 6–8, an alternative embodiment of an absorbent article 78 is depicted in which a two layered absorbent article 78 is shown. The absorbent article 78 is an elongated member having a longitudinal axis x—x, a transverse axis y—y and a vertical axis z—z. The absorbent article 78 can have a rectangular, hourglass, racetrack, oval, elliptical or other geometrical configuration when viewed from the top. The absorbent article 78 has a length, measured parallel to the longitudinal axis x—x, of less than about 500 millimeters (mm). Desirably, the absorbent article 78 has a length of less than about 400 mm, and most desirably, a length of less than about 350 mm. The absorbent article 78 has a crotch width, measured parallel to the transverse axis y—y, of less than about 150 mm. Desirably, the crotch width of the absorbent article 78 is less than about 125 mm, and most desirably, the crotch width of the absorbent article 78 is less than about 110 mm. It should be noted that the absorbent article 78 could have a wider width when measured away from the crotch region. The absorbent article 78 has a height, measured parallel to the vertical axis z—z of from about 2 mm to about 25 mm, and preferably, less than about 18 mm.

The absorbent article 78 contains an absorbent core 80 enclosed by a wrapper 82. The absorbent core 80 includes a first absorbent layer 84 and a second absorbent layer 86. The absorbent core 80 can be made from the same materials as the absorbent 12. Two desirable absorbent materials are wood pulp fluff and coform.

A superabsorbent is normally added to the absorbent core 80 to increase the amount of fluid that the absorbent core 80 can absorb and retain. The fluid retention capacity, also referred to as fluid absorbent capacity, of the absorbent core 80, for urine, should be at least 150 grams (g). Desirably, the fluid absorbent capacity of the absorbent core 80 for urine is at least 200 g. Most desirably, the fluid absorbent capacity of the absorbent core 16 for urine is at least 250 g.

In FIG. 8, the first absorbent layer 84 is positioned below a portion of the wrapper 82. The first absorbent layer 84 can optionally contain a hydrocolloidal material 88, commonly referred to as a superabsorbent. The superabsorbent 88 can be identical or similar to the superabsorbent 20.

The superabsorbent 88 that can be added to the absorbent core 80 can be produced to have almost any physical form. The superabsorbent 88 can be similar or different from the superabsorbent 20. Likewise, the superabsorbent 88 can be obtained from the same suppliers as recited earlier with reference to the superabsorbent 20.

It should also be noted that the absorbent core 80 could optionally be formed as a laminate structure with the superabsorbent 88 incorporated therein.

Still referring to FIG. 8, the absorbent article 78 includes a tissue 90 that is C-folded around the first absorbent layer 84. The tissue 90 functions to retain the superabsorbent 88 therein. It is advantageous to utilize in excess of about 15 percent by weight of superabsorbent 88 in the first absorbent layer 84. Preferably, at least about 20 percent by weight of the superabsorbent 88 is present in the first absorbent layer 84. Most preferably, about 24 percent by weight of the superabsorbent 88 is present in the first absorbent layer 84. The use of this percentage by weight of the superabsorbent 88 will significantly increase both the fluid absorbing and retention capacity of the absorbent core 80.

It should be noted the superabsorbent 88 does not have to be present in the first absorbent layer 84. However, one must recognize that the absorbent capacity of the first absorbent layer 84 will be less if no superabsorbent is present. When one uses a concentration of superabsorbent in the first absorbent layer 84 in excess of about 15 percent by weight, it is advantageous to wrap the first absorbent layer 84 in the tissue 90 to prevent the fine superabsorbent particles from falling out. If no superabsorbent 88 is present or if the superabsorbent 88 represents less than about 15 percent by weight of the first absorbent layer 84, then the tissue 90 could be eliminated.

The second absorbent layer 86 is located vertically below the first absorbent layer 84. The second absorbent layer 86 can also contain a hydrocolloidal material 92, commonly referred to as a superabsorbent. The superabsorbent 92 can be similar or different from the superabsorbent 88. However, from a cost and manufacturing standpoint, the superabsorbents 88 and 92 should be identical. The superabsorbent 92 can also be in particle form having a major dimension of less than about 500 microns. Such superabsorbents are commercially available from the vendors described above.

It has been found that the second or lower absorbent layer 86 can contain a lower, equal or greater percentage by weight of superabsorbent than the first absorbent layer 84. Preferably, the percentage by weight of the superabsorbent 92 in the second absorbent layer 86 will be less than the percentage by weight (excess of about 15 percent) of the superabsorbent 88 in the first absorbent layer 84. More preferably, the percentage by weight of the superabsorbent 92 in the second absorbent layer 86 will be less than about 12 percent by weight, most preferably, about 10 percent by weight. Since the percentage by weight of the superabsorbent 92 in the second absorbent layer 86 represents less than about 15 percent by weight of the second absorbent layer 86, it is not necessary to wrap the second absorbent layer 86 in tissue. As noted above with reference to the first absorbent layer 84, it is not necessary to include superabsorbent in the second absorbent layer 86. However, the absence of the superabsorbent 92 will decrease the fluid absorbent and retention capacity of the second absorbent layer 86.

It should be noted that even though the absorbent core 80 is described as including two absorbent layers 84 and 86, it could be formed from three or more absorbent layers, if desired.

Still referring to FIG. 8, an impediment layer 94 is positioned vertically below the second absorbent layer 86. The impediment layer 94 is aligned along the longitudinal axis x—x and lies between the absorbent core 80 and the wrapper 82. The impediment layer 94 is capable of slowing or blocking the downward movement of body fluid from the absorbent core 80 to the wrapper 82. The impediment layer 94 acts as a barrier that prevents the body fluid from passing directly through it. Instead, the body fluid is forced to flow around the edges of the impediment layer 94 in order to contact the wrapper 82. The impediment layer 94 can be formed from almost any type of liquid-impermeable material. A thermoplastic film is a good liquid-impermeable material that can be used to form the impediment layer 94. The thermoplastic film can be formed from polyethylene, polypropylene or a combination thereof. A polyethylene film having a thickness of less than about 2 mm works well.

It is also possible to form the impediment layer 94 from an adhesive, a polymer coating, a polyethylene sheet or from some other impervious material. For example, the adhesive or polymer coating could be sprayed or applied onto a portion of the entire lower surface of the second absorbent layer 86. By spraying or applying a thin adhesive or coating onto a portion of the second absorbent layer 86, an impediment layer 94 can be obtained. The adhesive or coating can be applied in liquid form such that a variety of impervious patterns or areas can be covered. The adhesive or coating can be self adhering and does not required another means for attaching it to the second absorbent layer 86. The adhesive or coating can be colored, if desired, to identify it from a non-coated surface. Desirably, the adhesive or coating is aligned along at least the central longitudinal portion of the wrapper 82. However, the pattern of adhesive or coating can take on almost any desired design, including multiple discrete shapes independently arranged over at least a portion of the exterior surface 118.

The impediment layer 94 can be positioned between the absorbent core 80 and the liquid permeable wrapper 82. Desirably, the impediment layer 94 is positioned below the second absorbent layer 86. When the impediment layer 94 is a polyethylene sheet, it should be positioned along the longitudinal centerline x—x and be below the second absorbent layer 82.

The absorbent core 80 has a height, measured parallel to the vertical axis z—z, of from about 2 mm to about 25 mm. Preferably, the absorbent core 80 has a height of from about 3 mm to about 20 mm. Most preferably, the absorbent core 80 has a height of from about 4 mm to about 15 mm. As the height of the absorbent core 80 increases, the fluid capacity of the absorbent core 80 normally increases. However, one should understand that the materials from which the absorbent core 80 is constructed, the presence of the superabsorbent 88 and/or 92, and the thickness of the absorbent core 80 will all determine the fluid capacity of the absorbent core 80.

Returning to FIGS. 6–8, the liquid permeable wrapper 82 encloses the absorbent core 80. The wrapper 82 will contact the genital area of the wearer when the absorbent article 78 is fitted against the wearer's torso. The wrapper 82 functions to direct such body fluid downward into the absorbent core 80. The liquid permeable wrapper 82 can be constructed from the same or similar material as taught above for the wrapper 14. A preferred material for the wrapper 82 is spunbond.

The wrapper 82 can also be formed from a material having a variety of basis weights. When the wrapper 82 is formed from spunbond, the material should have a basis weight of from about 0.3 ounces per square yard (osy) to about 1.0 osy. Preferably, the basis weight for the spunbond material is from about 0.3 osy to about 0.5 osy. Most preferably, the basis weight of the spunbond material should be about 0.385 osy.

The liquid permeable wrapper 82 should allow body fluids, especially urine, that contacts it to readily and quickly pass therethrough. In this regard, the material from which the wrapper 82 is constructed is selected to have pores or openings that permit liquids and/or gases to pass therethrough. The liquid permeability of the wrapper 82 can be measured using a standard test known to those skilled in the art.

Still referring to FIGS. 6–8, the liquid permeable wrapper 82 has a first end 96 spaced apart from and a second end 98. The liquid permeable wrapper 82 also has a first side edge 100 spaced apart from a second side edge 102, see FIG. 8. The wrapper 82 can be C-folded around the absorbent core 80 and the impediment layer 94 such that the second side edge 102 overlaps the first side edge 100, as shown. Alternatively, the first and second side edges, 100 and 102 respectively, can abut one another, if desired. It should be noted that the C-fold is aligned along the longitudinal axis x—x and the first and second side edges, 100 and 102 respectively, are aligned approximately parallel to the longitudinal axis x—x.

Referring to FIG. 8, the wrapper 82 can be secured to itself, to one or more surfaces of the absorbent core 80 and/or to the impediment layer 94 by a construction adhesive 104. In FIG. 8, the construction adhesive 104 is shown securing the wrapper 82 to the lower surface of both the second absorbent layer 86 and the impediment layer 94. The construction adhesive 104 can be a hot melt adhesive such as Huntsman REXTAC® RT 2730. Huntsman REXTAC® RT 2730 is commercially available from Huntsman Polymers Corporation having a mailing address of P.O. Box 371263 Pittsburgh, Pa. 15251-7263.

Referring again to FIG. 6 and 7, one will notice that the absorbent core 80 has a length, measured parallel to the longitudinal axis x—x, that is shorter than the length of the wrapper 82. This is important for it is necessary for the wrapper 82 to completely enclose the absorbent core 80 and form an integral product. When the absorbent article 78 includes an absorbent core 80 having superabsorbent particles 88 and/or 92 contained therein, the wrapper 82 will ensure than the superabsorbent particles 88 and/or 92 can not be released. The first and second ends, 96 and 98 respectively, of the absorbent article 78 will extend beyond the length of the absorbent core 80 and each end 96 and 98 is sealed. An ultrasonic bond can be used to seal the ends 96 and 98 of the wrapper 82. Other methods of sealing the first and second ends, 96 and 98 respectively, together can be used including forming a pressure bond, a heat bond, a heat and pressure bond, using a hot or cold melt adhesive, using thread, etc. These and other methods are known to those skilled in the art.

In FIGS. 6 and 7, a first seal 106 is formed at the first end 96 of the wrapper 82 by using adhesives or ultrasonics. The first seal 106 can have a variety of bond patterns. However, the bond pattern of the first seal 106 should have a dimension, measured along the longitudinal axis x—x, of from about 10 millimeters (mm) to about 30 mm. More preferably, the bond pattern of the first seal 106 will have a dimension, measured along the longitudinal axis x—x of from about 12 mm to about 25 mm. Most preferably, the bond pattern of the first seal 106 will have a dimension, measured along the longitudinal axis x—x, of from about 15 mm to about 20 mm.

A second seal 108 is formed at the second end 98 of the wrapper 82 by using adhesives or ultrasonics. The second seal 108, like the first seal 106, can have a variety of bond patterns. However, the bond pattern of the second seal 108 should have a dimension, measured along the longitudinal axis x—x, of from about 10 millimeters (mm) to about 30 mm. More preferably, the bond pattern of the second seal 108 will have a dimension, measured along the longitudinal axis x—x, of from about 12 mm to about 25 mm. Most preferably, the bond pattern of the second seal 108 will have a dimension, measured along the longitudinal axis x—x, of from about 15 mm to about 20 mm. It should be noted that the bond pattern on the first and second seals 106 and 108 should be identical. However, such bond patterns can be made to be different, if desired.

Figure 9:
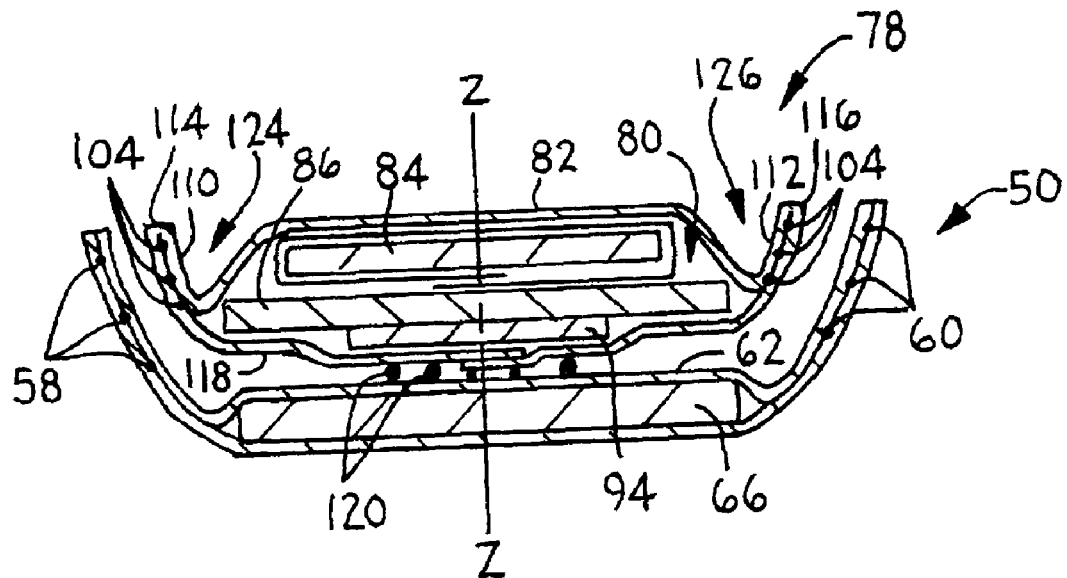
FIG. 9 is a cross-sectional view of an absorbent article and an absorbent undergarment depicting the upstanding side walls of the absorbent article forming a pair of reservoirs positioned adjacent to the absorbent core.

Referring now to FIGS. 8–9, one will notice that the wrapper 82 has a pair of fringes 110 and 112 which extends laterally outward from each longitudinal side of the second absorbent layer 86. Each of the pair of fringes 110 and 112 runs the entire length of the absorbent article 78. Each of the pair of fringes 110 and 112 has a width dimension, measured parallel to the transverse axis y—y that extends laterally outward from one of the longitudinal sides by a distance of at least 10 mm. Preferably, each of the pair of fringes 110 and 112 has a width dimension that extend laterally outward from one of the longitudinal sides by a distance of from about 10 mm to about 30 mm. More preferably, each of the pair of fringes 110 and 112 has a width dimension that extend laterally outward from one of the longitudinal sides by a distance of from about 12 mm to about 20 mm. The pair of fringes 110 and 112 are capable of being biased upward to form a pair of upstanding side walls 114 and 116, see FIG. 9.

One will notice that the pair of fringes 110 and 112 do not contain any elastic components, such as elastic threads, strands, etc. Another way of expressing this is to say that the pair of fringes 110 and 112 are free or void of any elastic. One reason for this is that the pair of fringes 110 and 112 do not require elastic materials to make them act as upstanding side walls.

As the absorbent article 78 is secured to the bodyside cover 62 of the primary absorbent undergarment 50, it acquires a cup shape or curvature due to the configuration of the primary absorbent undergarment 50. This cup shape or curvature causes the pair of fringes 110 and 112 to be biased upward and forms the pair of upstanding side walls 114 and 116. Each of the side walls, 114 and 116 respectively, is free of elastics. It is not necessary that stretchable material or material that can extend or contract in at least one direction be present in the side walls 114 and 116 in order to make the side walls 114 and 116 stand upright. The combination of the curvature of the crotch portion 68 of the primary absorbent undergarment 50 and the width dimension of each of the fringes 110 and 112 allow the pair of side walls 114 and 116 to acquire an upright orientation.

The pair of fringes 110 and 112 also do not have to be stiff in order to stand up. The pair of fringes 110 and 112 may contain one or more beads, lines or strips of the construction adhesive 104. The construction adhesive 104 is primarily used to maintain the relatively flat shape of the pair of fringes 110 and 112.

As shown in FIGS. 8 and 9, the wrapper 82 is the only material, except for the construction adhesive 104, that forms the pair of fringes 110 and 112. By folding or doubling the wrapper 82 upon itself, the pair of fringes 110 and 112 are formed. The pair of fringes 110 and 112 are very flexible, pliable and bendable. The pair of fringes 110 and 112 are also receptive to acquiring an upward configuration when placed in at least a portion of the crotch portion 68 of the primary absorbent undergarment 50.

Still referring to FIGS. 8 and 9, the wrapper 82 has a lower exterior surface 118. An attachment means 120 is formed on or secured to the exterior surface 118. The attachment means 120 is preferably a garment adhesive. Other forms of attachment mechanisms can also be used, such as hook and/or loop fasteners, tape, glue, etc. VELCRO® is one form of a hook fastener that engages a loop material. VELCRO® is a registered trademark of Velcro Industries having a mailing address of 406 Brown Avenue, Manchester, N.H. 03103. When the attachment means 120 is a garment adhesive, the adhesive can be either a hot or cold melt adhesive that is sprayed, brushed, slot coated or otherwise secured onto the exterior surface 118 of the wrapper 82. The garment adhesive can be applied as one or more lines or strips of adhesive aligned approximately parallel to the longitudinal axis x—x. Preferably, the garment adhesive is a hot melt adhesive. Garment adhesive is commercially available from several vendors. One such vendor is National Starch Co. having an office at 10 Finderne Avenue, Bridgewater, N.J. 08807.

A releasable peel strip 122 can be positioned over the attachment means 120. The releasable peel strip 122 protects the attachment means 120 from contamination prior to use of the absorbent article 78 by the consumer. The releasable peel strip 122 is designed to be removed by the consumer just prior to positioning and attaching the absorbent article 78 to the crotch portion of a primary absorbent undergarment. The peel strip 122 is generally slightly larger in overall dimensions than the attachment means 120 so as to avoid registration problems when the absorbent article 78 is being manufactured. The use of a slightly larger dimensioned peel strip 122 to cover the attachment means 120 is particularly advantageous when the absorbent article 78 is being produced at relatively high speeds. By "high speeds" is meant the ability to manufacture at a speed of more than 200 absorbent articles per minute. The peel strip 122 can be a white Kraft paper, coated on one side by silicone so that it can be easily released from the attachment means 120.

Returning to FIG. 7, one will notice that the peel strip 122 extends the entire length of the absorbent article 78. By sizing the peel strip 122 to have the same length as the absorbent article 78, one can increase manufacturing speeds. The reason for this is that the peel strip 122 and the absorbent article 78 can be cut together and one does not have to register or center the overall length of the peel strip 122 onto the absorbent article 78. However, one can use a shorter peel strip, if desired. The use of a shorter length of peel strip 122 can reduce the cost of the material needed to form the absorbent article 78.

The absorbent article 78 can be secured to the primary absorbent undergarment 50, as described above with reference to the absorbent article 10.

The absorbent article 78 is attached to the bodyside cover 62 of the primary absorbent undergarment 50 by the attachment means 120. Usually, the wearer will place or position the crotch portion of the absorbent article 78 over at least a portion of the crotch portion 68 of the primary absorbent undergarment 50. The comfort to the wearer and the location where the body fluid is most likely to insult the absorbent article 78 will dictate the exact placement of the absorbent article 78 in the undergarment 50. The primary absorbent undergarment 50 can be positioned onto the consumer's legs and pulled up around the torso of the wearer. For example, the absorbent article 78 can be attached to the primary absorbent undergarment 50 before the undergarment 50 is positioned onto the wearer. Alternatively, the absorbent article 78 can be attached to the primary absorbent undergarment 50 when the undergarment 50 is positioned about the shins, knees or thighs of the wearer. Still further, it is also possible for a caregiver to position the primary absorbent undergarment 50, in an open configuration, about the wearer's torso and then attach the absorbent article 78 before the primary absorbent undergarment 50 is closed and/or fastened around the wearer's waist.

Each of the pair of upstanding side walls 114 and 116 forms a reservoir, 124 and 126 respectively, located adjacent to and outward from the absorbent core 80. The pair of reservoirs 124 and 126 are capable of retaining body fluid that has run off of the wrapper 82 until the body fluid can be absorbed by the first absorbent layer 84. The construction of the absorbent article 78 and the width dimension of the pair of fringes 110 and 112 will dictate the depth of each of the pair of reservoirs 124 and 126. The pair of fringes 110 and 112 can be sized to be less than, equal to or greater than the height of the absorbent core 80. In FIG. 9, each of the pair of side walls 114 and 116 have sufficient height to hold body fluid that pooled on the wrapper 82 and has run laterally off to one or both sides. The pair of reservoirs 124 and 126 should also have a length that extends along at least the middle of the absorbent article 78 when measured along the longitudinal axis x—x. Desirably, each of the pair of reservoirs 124 and 126 will have a length that extends along a portion of the length of the absorbent 78. Depending upon the size of the absorbent article 78, each of the pair of reservoirs 124 and 126 should have a length of greater than about 1 inch (about 25.4 mm). More desirably, each of the pair of reservoirs 124 and 126 should have a length of greater than about 2 inches (about 51 mm). Most desirably, each of the pair of reservoirs 124 and 126 should have a length of greater than about 3 inches (about 76 mm).

The absorbent article 78 can be visualized as an absorbent structure that is used to extend or prolong the useful life of the primary absorbent undergarment 50. Since the primary absorbent undergarment 50 is more costly than the absorbent article 78, the consumer can extend the life of the primary absorbent article 50 for a relatively small amount of money. It is also possible for the consumer to sequentially change the original absorbent article 78, when wetted, with another absorbent article 78. This will enable the wearer to extend the time period before the primary absorbent undergarment 50 becomes so saturated with urine that it needs to be discarded. It is also possible to insert two or more absorbent articles 78 into the undergarment 50 at the same time. This will further extend the life of the undergarment 50.

It should be noted that the purpose of the absorbent article 78 is to receive and retain body fluid, especially urine. The absorbent article 78 is constructed with a liquid permeable wrapper 82 so as to permit urine to pass quickly down into the absorbent core 80. Excess urine that cannot be retained by the absorbent core 80 and/or the superabsorbents 88 and 92 will move downward through that portion of the wrapper 82 that is located below the absorbent core 80. This excess urine will then contact the primary absorbent undergarment 50 and be retained therein. However, if the absorbent article 78 is insulted with urine at a very slow rate, the absorbent article 78 may be able to absorb and retain essentially all of the urine expelled from the wearer. In this situation, the wearer can remove the initial absorbent article 78 that has become saturated and replace it with another dry absorbent article 78. By doing so, the wearer will extend the wearing time of the primary absorbent undergarment 50.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. An absorbent article comprising:
a) in absorbent having first and second longitudinal sides; and
b) a liquid permeable wrapper enclosing said absorbent, said wrapper extending laterally outward from each of said first and second longitudinal sides a distance of at least about 10 millimeters to form a pair of fringes capable of being biased upward to form a pair of upstanding side walls when placed in an undergarment, said upstanding wide wails forming a pair of reservoirs located adjacent to sold absorbent which retain body fluid that has run off of said wrapper until said body fluid can be absorbed by said absorbent; wherein each of said pair of fringes runs the entire length of said article;

each of the fringes is provided by doubled regions of maid wrapper;

each doubled region of sold wrapper provides a fringe width which extends beyond its corresponding first or second longitudinal side of said absorbent;

each doubled region of said wrapper is attached together across its fringe width with construction adhesive; and both of said fringes are entirely void of any elastics.

2. The absorbent article of claim 1 wherein each of said pair of fringes extends from about 10 mm to about 30 mm beyond said first and second longitudinal sides of said absorbent.

3. The absorbent article of claim 1 further comprising an impediment layer positioned below said absorbent and between said absorbent and maid wrapper; wherein said impediment layer includes a liquid-impermeable film; and said film has a width that is less than a width of said absorbent.

4. The absorbent article of claim 1 wherein said wrapper has first and second side edges and is C-folded around said absorbent such that said second side edge overlaps said first side edge.

5. The absorbent article of claim 1 wherein said wrapper has first and second side edges and is C-folded around said absorbent such that said second side edge abuts said first side edge.

6. The absorbent article of claim 1 wherein said wrapper is spunbond and has a basis weight of from about 0.3 osy to about 1.0 osy.

7. The absorbent article of claim 1 wherein said wrapper has first and second spaced apart ends which extend beyond said absorbent and each end is sealed to further enclose said absorbent.

8. An absorbent article comprising:
a) an absorbent having first and second longitudinal sides; and
b) a liquid permeable wrapper enclosing said absorbent, said wrapper extending laterally outward from each of said first and second longitudinal sides a distance of at least about 10 milliliters to from a pair of fringes capable of being biased upward to from a pair of upstanding side walls when placed in an undergarment, said upstanding side walls forming a pair of reservoirs located adjacent to said absorbent which retain body fluid that has run off of said wrapper until said body fluid can be absorbed by said absorbent; wherein each of said pair of fringes runs the entire length of said article;

each of the fringes is provided by doubled regions of said wrapper;

each doubled region of said wrapper provides a fringe width which extends beyond its corresponding first or second longitudinal side of said absorbent;

each doubled region of said wrapper is attached together across its fringe width with construction adhesive; and said absorbent has a height of at least about 10 mm and said each of said pair of upstanding side walls extend above the height of said absorbent when placed in an undergarment.

9. An absorbent article comprising:

a) an absorbent having first and second longitudinal sides; and b) a liquid permeable wrapper having first and second side edges, said wrapper being C-folded around said absorbent such that said wrapper encloses the absorbent, said wrapper extending laterally outward from each of said first and second longitudinal sides a distance of at least about 10 millimeters to form a pair of fringes capable of being biased upward to form a pair of upstanding side walls when placed in an undergarment, both of said fringes entirely void of any elastics, and said upstanding side walls forming a pair of reservoirs located adjacent to said absorbent which retain body fluid that has run off of said wrapper until said body fluid can be absorbed by said absorbent.

10. The absorbent article of claim 9 wherein said absorbent has a height of at least about 10 mm and each of said pair of upstanding side walls extend above the height of said absorbent when placed in an undergarment.

11. The absorbent article of claim 9 wherein a liquid-impermeable impediment layer is positioned between said absorbent and said liquid permeable wrapper and is formed from an adhesive.

12. The absorbent article of claim 9 wherein a liquid-impermeable impediment layer is positioned between said absorbent and said liquid permeable wrapper and is a polyethylene sheet.

13. The absorbent article of claim 9 wherein said wrapper has en exterior surface; a hook fastener is secured to the exterior surface of said wrapper; and said hook fastener is configured to attach said absorbent article to a crotch portion of a primary absorbent undergarment.

14. The absorbent article of claim 9 wherein said wrapper has an exterior surface; an adhesive attachment means is secured to the exterior surface of said wrapper; and said adhesive attachment means is configured to attach said absorbent article to a crotch portion of a primary absorbent undergarment.

15. An absorbent article comprising:

a) an absorbent having first and second longitudinal sides;

b) a liquid permeable wrapper having first and second spaced apart ends and first and second side edges, said wrapper being C-folded around said absorbent such that said second side edge overlaps said first side edge and said first and second spaced apart ends extend beyond said absorbent and each end is sealed to enclose said absorbent, said wrapper extending laterally outward from each of said first and second longitudinal sides a distance of at least about 10 millimeters to form a pair of fringes capable of being biased upward to form a pair of upstanding side wails when placed in an undergarment, said upstanding side walls forming a pair of reservoirs located adjacent to said absorbent which retain body fluid that has run off of said wrapper until said body fluid can be absorbed by said absorbent; and c) an attachment means secured to a lower exterior surface of sold wrapper, said attachment means configured to attach said absorbent article to a crotch portion of a primary absorbent undergarment;

wherein both of said fringes are entirely void of any elastic.

16. The absorbent article of claim 15 further comprising an impediment layer positioned below said absorbent and enclosed by said wrapper, said impediment layer being capable of slowing the downward movement of body fluid from said absorbent and including a liquid-impermeable film; and said film having a width that is less than a width of said absorbent.

17. The absorbent article of claim 15 wherein said absorbent includes at least two absorbent layers.

18. The absorbent article of claim 17 wherein each of said absorbent layers contains a superabsorbent.

19. The absorbent article of claim 15 wherein said absorbent includes first and second absorbent layers and said first absorbent layer contains a higher percentage of superabsorbent than said second absorbent layer.

20. The absorbent article of claim 1 wherein said wrapper has a lower exterior surface; an attachment means is secured to the exterior surface of said wrapper; and said attachment means is configured to attach said absorbent article to a crotch portion of a primary absorbent undergarment.

* * * * *